(12) United States Patent
Lewis

(10) Patent No.: US 10,632,455 B2
(45) Date of Patent: *Apr. 28, 2020

(54) HIGH CHARGE DENSITY METALLOPHOSPHATE MOLECULAR SIEVES

(71) Applicant: UOP LLC, Des Plaines, IL (US)

(72) Inventor: Gregory J. Lewis, Santa Cruz, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/123,927

(22) Filed: Sep. 6, 2018

(65) Prior Publication Data

US 2019/0009258 A1     Jan. 10, 2019

Related U.S. Application Data

(63) Continuation of application No. PCT/US2017/032597, filed on May 15, 2017.

(60) Provisional application No. 62/341,193, filed on May 25, 2016.

(51) Int. Cl.
| | | |
|---|---|---|
| *B01J 29/84* | (2006.01) | |
| *C01B 39/54* | (2006.01) | |
| *C07D 245/02* | (2006.01) | |

(52) U.S. Cl.
CPC ............. *B01J 29/84* (2013.01); *C01B 39/54* (2013.01); *C07D 245/02* (2013.01); *Y02P 30/42* (2015.11)

(58) Field of Classification Search
CPC .......... B01J 20/0222; B01J 20/0225; B01J 20/0244; B01J 20/0292; B01J 20/048; B01J 39/12; B01J 39/02; B01J 37/10; B01J 37/06; B01J 37/009; B01J 29/84; B01J 20/3085; B01J 20/3078; B01J 20/3071; B01J 37/04; C01B 39/54; C10G 45/04; C10G 45/06; C10G 47/125; C10G 11/04; C10G 45/60

See application file for complete search history.

(56) References Cited

U.S. PATENT DOCUMENTS 10,159,964 B2 * 12/2018 Lewis .................... C10G 45/04
10,159,965 B2 * 12/2018 Lewis .................... B01J 20/048

OTHER PUBLICATIONS

Feng et al., (Hydrothermal syntheses and structural characterization of zeolite analogue compounds based on cobalt phosphate, Nature, 1997, vol. 388, pp. 735-740).*

* cited by examiner

*Primary Examiner* — Jafar F Parsa

(57) ABSTRACT

A new family of highly charged crystalline microporous metallophosphate molecular sieves designated MeAPO-81 has been synthesized. These metallophosphates are represented by the empirical formula of:

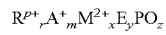

$R^{p+}{}_r A^+{}_m M^{2+}{}_x E_y PO_z$ where A is an alkali metal such as potassium, R is at least one quaternary ammonium cation of which one must be a cyclic diquaternary organoammonium cation such as N,N,N',N'-tetramethyl-N,N'-butano-1,6-hexanediammonium, M is a divalent metal such as zinc and E is a trivalent framework element such as aluminum or gallium. The MeAPO-81 family of materials has the BPH topology. The MeAPO-81 family of materials is among the first MeAPO-type molecular sieves to be stabilized by combinations of alkali and organoammonium cations, enabling unique high charge density compositions. The MeAPO-81 family of molecular sieves has catalytic properties for carrying out various hydrocarbon conversion processes and separation properties for separating at least one component.

7 Claims, No Drawings

HIGH CHARGE DENSITY METALLOPHOSPHATE MOLECULAR SIEVES

CROSS-REFERENCE TO RELATED APPLICATIONS

This application is a Continuation of copending International Application No. PCT/US2017/032597 filed May 15, 2017, which application claims priority from U.S. Provisional Application No. 62/341,193 filed May 25, 2016, the contents of which cited applications are hereby incorporated by reference in their entirety.

FIELD OF THE INVENTION

This invention relates to a family of charged metallophosphate-based molecular sieves designated MeAPO-81. They are represented by the empirical formula of:

$$R^{p+}_r A^+_m M^{2+} E_y PO_z$$

where A is an alkali metal such as potassium, R is at least one quaternary ammonium cation of which one must be a cyclic diquaternary organoammonium cation such as N,N,N',N'-tetramethyl-N,N'-butano-1,6-hexanediammonium, M is a divalent metal such as zinc and E is a trivalent framework element such as aluminum or gallium. The MeAPO-81 family of materials has the BPH topology.

BACKGROUND OF THE INVENTION

Zeolites are crystalline aluminosilicate compositions which are microporous and which are formed from corner sharing $[AlO_{4/2}]^-$ and $SiO_{4/2}$ tetrahedra. Numerous zeolites, both naturally occurring and synthetically prepared are used in various industrial processes. Synthetic zeolites are prepared via hydrothermal synthesis employing suitable sources of Si, Al and structure directing agents (SDAs) such as alkali metals, alkaline earth metals, amines, or organoammonium cations. The structure directing agents reside in the pores of the zeolite and are largely responsible for the particular structure that is ultimately formed. These species balance the framework charge associated with aluminum and can also serve as space fillers. Zeolites are characterized by having pore openings of uniform dimensions, having a significant ion exchange capacity, and being capable of reversibly desorbing an adsorbed phase which is dispersed throughout the internal voids of the crystal without significantly displacing any atoms which make up the permanent zeolite crystal structure. Zeolites can be used as catalysts for hydrocarbon conversion reactions, which can take place on outside surfaces of the zeolite as well as on internal surfaces within the pores of the zeolite.

In 1982, Wilson et al. developed aluminophosphate molecular sieves, the so-called AlPOs, which are microporous materials that have many of the same properties of zeolites, but are silica free, composed of $[AlO_{4/2}]^-$ and $[PO_{4/2}]^+$ tetrahedra (see U.S. Pat. No. 4,319,440). Subsequently, charge was introduced to the neutral aluminophosphate frameworks via the substitution of $SiO_{4/2}$ tetrahedra for $[PO_{4/2}]^+$ tetrahedra to produce the SAPO molecular sieves (see U.S. Pat. No. 4,440,871).

Another way to introduce framework charge to neutral aluminophosphates is to substitute $[M^{2+}O_{4/2}]^{2-}$ tetrahedra for $[AlO_{4/2}]^-$ tetrahedra, which yield the MeAPO molecular sieves (see U.S. Pat. No. 4,567,029). In that work, examples of MeAPO materials were limited to relatively low substitution of $Me^{2+}$ for $Al^{3+}$, as materials with the highest $Me^{2+}$ incorporation exhibited Me/Al ratios of about 0.4. It is furthermore possible to introduce framework charge on AlPO-based molecular sieves via the introduction both of $SiO_{4/2}$ and $[M^{2+}O_{4/2}]^{2-}$ tetrahedra to the framework, giving MeAPSO molecular sieves (see U.S. Pat. No. 4,973,785).

In the early 1990's, high charge density molecular sieves, similar to the MeAPOs but without the Al, were developed by Bedard (see U.S. Pat. No. 5,126,120) and Gier (see U.S. Pat. No. 5,152,972). These metal phosphates (sometimes arsenates, vanadates) were based on $M^{2+}$ (M=Zn, Co), the general formula of which, in terms of the T-atoms, $T^{2+}-T^{5+}$, was approximately $A^+T^{2+}T^{5+}O_4$, having framework charge densities similar to Si/Al=1 zeolites and were charge balanced by alkali cations, $A^+$, in the pores. Later attempts to prepare metallophosphates of similar compositions but with organic SDAs led to porous, but interrupted structures, i.e., the structures contained terminal P—O—H and Zn—N bonds (see J. Mater. Chem., 1992, 2(11), 1127-1134). Attempts at Al substitution in a zincophosphate network was carried out in the presence of both alkali and organoammonium agents, specifically the most highly charged organoammonium species, tetramethylammonium, but because of the high framework charge density, only the alkali made it into the pores to balance framework charge (see U.S. Pat. No. 5,302,362). Similarly, in a high charge density zincophosphate system that yielded the zinc phosphate analog of zeolite X, the synthesis in the presence of $Na^+$ and $TMA^+$ yielded a product that contained considerably less $TMA^+$ than $Na^+$ (See Chem. Mater., 1991, 3, 27-29).

To bridge the rather large charge density gap between the lower charge density MeAPOs of U.S. Pat. No. 4,567,029 and the aforementioned high charge density alkali-stabilized $Me^{2+}$-phosphates of Bedard and Gier, Stucky's group developed a synthesis route using amines, usually diamines, in ethylene glycol-based reaction mixtures. They were able to make high charge density, small pore MeAPOs in which the concentrations of $Co^{2+}$ and $Al^{3+}$ in $R(Co_xAl_{1-x})PO_4$ were varied such that $0.33 \le x \le 0.9$ in the so-called ACP series of materials, the aluminum cobalt phosphates (see Nature, 1997, 388, 735). Continuing with this synthesis methodology utilizing ethylene glycol solvent and matching the amines to framework charge densities for $R(M^{2+}_xAl_{1-x})PO_4$, such that $0.4 \le x \le 0.5$, ($M^{2+}=Mg^{2+}$, $Mn^{2+}$, $Zn^{2+}$, $Co^{2+}$) the large pore materials UCSB-6, -8 and -10 were isolated (see Science, 1997, 278, 2080). Crystal dimensions isolated from that work were often on the order of hundreds of microns. This approach also yielded MeAPO analogs of zeolite rho of the composition where $RM^{2+}_{0.5}Al_{0.5}PO_4$, where R=N,N'-diisopropyl-1,3-propanediamine, $M^{2+}$=$Mg^{2+}$, $Co^{2+}$ and $Mn^{2+}$. The reliance of this synthesis approach on an ethylene glycol solvent does not lend itself well to industrial scale, from both a safety and environmental point of view. While several others embraced Stucky's approach, there has been little activity in this intermediate charge density region, where $0.2 \le x \le 0.9$ for the $[M^{2+}_xAl_{1-x}PO_4]^{x-}$ compositions.

Pursuing aqueous chemistry, Wright et al. used highly charged triquaternary ammonium SDAs to make new MeAPO materials (see Chem. Mater., 1999, 11, 2456-2462). One of these materials, STA-5 with the BPH topology, $(Mg_{2.1}Al_{11.9}P_{14}O_{28})$, exhibited significant substitution of $Mg^{2+}$ for $Al^{3+}$, up to about 15%, but less substitution than seen in Stucky's non-aqueous ethylene glycol approach.

More recently, Lewis et. al. developed aqueous solution chemistry using quaternary ammonium cations leading to high charge density SAPO, MeAPO, and MeAPSO materials, enabling greater substitution of $SiO_{4/2}$ and $[M^{2+}O_{4/2}]^{2-}$ into the framework for $[PO_{4/2}]^+$ and $[AlO_{4/2}]^-$, respectively, using the ethyltrimethylammonium (ETMA$^+$) and diethyldimethylammonium (DEDMA$^+$) SDAs. These materials include ZnAPO-57 (U.S. Pat. No. 8,871,178), ZnAPO-59 (U.S. Pat. No. 8,871,177), ZnAPO-67 (U.S. Pat. No. 8,697,927), and MeAPSO-64 (U.S. Pat. No. 8,696,886). The relationship between the increasing product charge densities and reaction parameters, namely the ETMAOH(DEDMAOH)/H$_3$PO$_4$ ratios, were outlined in the literature (see MICROPOROUS AND MESOPOROUS MATERIALS, 2014, 189, 49-63). For the MeAPO materials, the incorporation of M$^{2+}$ observed in these systems was such that for the formulation $[M^{2+}{}_xAl_{1-x}PO_4]^{x-}$, x~0.3.

Applicants have now synthesized a new family of highly charged metallophosphate framework materials, designated MeAPO-81, with higher charge densities than the MeAPOs of U.S. Pat. No. 4,567,029 and the MeAPO materials isolated by Lewis. These metallophosphates are prepared from aqueous solution utilizing a combination of quaternary ammonium and alkali cations. More specifically, at least one of the quaternary ammonium cations must be a cyclic diquaternary ammonium cation. The MeAPO-81 materials have the BPH topology (see Database of Zeolite Structures, www.iza-structure.org/databases) and have much higher metal content than the magnesioaluminophosphate STA-5 (Mg$_{2.1}$Al$_{11.9}$P$_{14}$O$_{28}$), another MeAPO that has the BPH topology (see CHEM. MATER., 1999, 11, 2456-2462.) The utility of alkali in MeAPO-based systems is uncommon and in combination with organoammonium cations under the conditions prescribed in this disclosure enables this system to achieve the higher charge densities and the desired midrange compositions between the low charge density MeAPO and high charge density Me$^{2+}$-phosphate extremes.

SUMMARY OF THE INVENTION

As stated, the present invention relates to a new family of metallophosphate molecular sieves designated MeAPO-81. Accordingly, one embodiment of the invention is a microporous crystalline material having a three-dimensional framework of $[M^{2+}O_{4/2}]^{2-}$, $[EO_{4/2}]^-$, and $[PO_{4/2}]^+$ tetrahedral units and an empirical composition in the as synthesized form and on an anhydrous basis expressed by an empirical formula of:

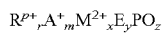
$$R^{p+}{}_rA^+{}_mM^{2+}{}_xE_yPO_z$$

where R is at least one quaternary organoammonium cation of which there must be at least one cyclic diquaternary organoammonium cation, the quaternary ammonium cations selected from the group consisting of N,N,N',N'-tetramethyl-N,N'-p-xyleno-1,6-hexanediammonium, N,N,N',N'-tetramethyl-N,N'-butano-1,6-hexanediammonium, N,N,N',N'-tetrmaethyl-N,N'-hexano-1,6-hexanediammonium, N,N,N',N'-tetraethyl-N,N'-hexano-1,5-pentanediammonium, N,N,N',N'-tetramethyl-N,N'-m-xyleno-1,6-hexanediammonium, N,N,N',N'-tetramethyl-N,N'-o-xyleno-1,2-ethylenediammonium, N,N,N',N'-tetramethyl-N,N'-butano-1,2-ethylenediammonium, N,N,N',N'-tetramethyl-N,N'-butano-1,2-ethylenediammonium, tetramethylammonium (TMA$^+$), ethyltrimethylammonium (ETMA$^+$), diethyldimethylammonium (DEDMA$^+$), methyltriethylammonium (MTEA$^+$), dipropyldimethylammonium (DPDMA$^+$), tetraethylammonium (TEA), tetrapropylammonium (TPA$^+$), tetrabutylammonium (TBA$^+$) and mixtures thereof, "r" is the mole ratio of R to P and has a value of about 0.04 to about 1.0, "p" is the weighted average valence of R and varies from 1 to 2, A is an alkali metal such as Li$^+$, Na$^+$, K$^+$, Rb$^+$ and Cs$^+$ and mixtures thereof, "m" is the mole ratio of A to P and varies from 0.1 to 1.0, M is a divalent element selected from the group of Zn, Mg, Co, Mn and mixtures thereof, "x" is the mole ratio of M to P and varies from 0.2 to about 0.9, E is a trivalent element selected from the group consisting of aluminum and gallium and mixtures thereof, "y" is the mole ratio of E to P and varies from 0.1 to about 0.8 and "z" is the mole ratio of O to P and has a value determined by the equation:

$$z=(m+p·r+2·x+3·y+5)/2$$

and is characterized in that it has the x-ray diffraction pattern having at least the d-spacings and intensities set forth in Table A:

TABLE A

| 2Θ | d(Å) | I/I$_0$ % |
|---|---|---|
| 6.83-6.64 | 12.94-13.30 | m-s |
| 7.69-7.49 | 11.48-11.80 | vs-vs |
| 10.12-10.02 | 8.73-8.82 | w |
| 13.24-13.01 | 6.68-6.80 | w-m |
| 14.90-14.63 | 5.94-6.05 | w-m |
| 15.48-15.34 | 5.72-5.77 | w-m |
| 16.70-16.45 | 5.305-5.385 | w |
| 18.99-18.67 | 4.67-4.75 | w-m |
| 20.31-20.07 | 4.37-4.42 | m-s |
| 21.32-21.01 | 4.165-4.225 | m-s |
| 23.97-23.64 | 3.71-3.76 | w-m |
| 24.33-24.00 | 3.655-3.705 | m-vs |
| 26.71-26.35 | 3.335-3.38 | m |
| 27.51-27.00 | 3.24-3.30 | w-m |
| 27.68-27.25 | 3.22-3.27 | w-m |
| 28.78-28.31 | 3.10-3.15 | w-m |
| 29.86-29.50 | 2.99-3.025 | m-s |
| 30.38-29.96 | 2.94-2.98 | m-s |
| 30.70-30.27 | 2.91-2.95 | m |
| 33.60-33.03 | 2.665-2.71 | m |
| 34.13-33.73 | 2.625-2.655 | m |
| 35.35-34.84 | 2.537-2.573 | w-m |

Another embodiment of the invention is a process for preparing the crystalline metallophosphate molecular sieve described above. The process comprises forming a reaction mixture containing reactive sources of R, A, M, E and P and heating the reaction mixture at a temperature of about 60° to about 200° C. for a time sufficient to form the molecular sieve, the reaction mixture having a composition expressed in terms of mole ratios of the oxides of:

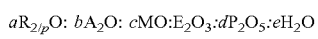
$$aR_{2/p}O: bA_2O: cMO:E_2O_3:dP_2O_5:eH_2O$$

where "a" has a value of about 2.1 to about 100, "b" has a value of about 0.1 to about 8.0, "c" has a value of about 0.25 to about 8, "d" has a value of about 1.69 to about 25, and "e" has a value from 30 to 5000.

Yet another embodiment of the invention is a hydrocarbon conversion process using the above-described molecular sieve as a catalyst. The process comprises contacting at least one hydrocarbon with the molecular sieve at conversion conditions to generate at least one converted hydrocarbon.

Still another embodiment of the invention is a separation process using the crystalline MeAPO-81 material. The process may involve separating mixtures of molecular species or removing contaminants by contacting a fluid with the MeAPO-81 molecular sieve. Separation of molecular species can be based either on the molecular size (kinetic diameter) or on the degree of polarity of the molecular species. Removing contaminants may be by ion exchange with the molecular sieve.

DETAILED DESCRIPTION OF THE INVENTION

Applicants have prepared a family of high charge density crystalline microporous metallophosphate compositions with the BPH topology, designated MeAPO-81. Compared to other early MeAPO materials, described in U.S. Pat. No. 4,567,029, the MeAPO-81 family of materials contains much more $M^{2+}$ and exhibits high framework (FW) charge densities that unlike these other MeAPOs, use alkali cations in addition to organoammonium ions to balance the FW charge. The instant microporous crystalline material (MeAPO-81) has an empirical composition in the as-synthesized form and on an anhydrous basis expressed by the empirical formula:

$$R^{p+}_r A^+_m M^{2+}_x E_y PO_z$$

where A is at least one alkali cation and is selected from the group of alkali metals. Specific examples of the A cations include but are not limited to lithium, sodium, potassium, rubidium, cesium and mixtures thereof. R is at least one quaternary ammonium cation, of which at least one of the quaternary ammonium cations must be a cyclic diquaternary ammonium cation, examples of which include but are not limited to N,N,N',N'-tetramethyl-N,N'-p-xyleno-1,6-hexanediammonium, N,N,N',N'-tetramethyl-N,N'-butano-1,6-hexanediammonium, N,N,N',N'-tetrmaethyl-N,N'-hexano-1,6-hexanediammonium, N,N,N',N'-tetraethyl-N,N'-hexano-1,5-pentanediammonium, N,N,N',N'-tetramethyl-N,N'-m-xyleno-1,6-hexanediammonium, N,N,N',N'-tetramethyl-N,N'-o-xyleno-1,2-ethylenediammonium, N,N,N',N'-tetramethyl-N,N'-butano-1,2-ethylenediammonium, N,N,N',N'-tetramethyl-N,N'-butano-1,2-ethylenediammonium, tetramethylammonium (TMA$^+$), ethyltrimethylammonium (ETMA$^+$), diethyldimethylammonium (DEDMA$^+$), methyltriethylammonium (MTEA$^+$), dipropyldimethylammonium (DPDMA$^+$), tetraethylammonium (TEA$^+$), tetrapropylammonium (TPA$^+$), tetrabutylammonium (TBA$^+$) and mixtures thereof, "r" is the mole ratio of R to P and varies from about 0.04 to about 1.0, while "p" is the weighted average valence of R and varies from about 1 to 2. M and E are tetrahedrally coordinated and in the framework, M is a divalent element selected from the group of Zn, Mg, Co, Mn and mixtures thereof, while E is a trivalent element selected from aluminum and gallium and mixtures thereof. The value of "m" is the mole ratio of A to P and varies from 0.1 to about 1.0, "x" is mole ratio of M to P and varies from 0.2 to about 0.9, while the ratio of E to P is represented by "y" which varies from about 0.10 to about 0.8. Lastly, "z" is the mole ratio of 0 to E and is given by the equation:

$$z=(m+r \cdot p+2 \cdot x+3 \cdot y+5)/2.$$

When only one type of R organoammonium cation is present, then the weighted average valence is just the valence of that cation, e.g., +1 or +2. When more than one R cation is present, the total amount of R is given by the equation:

$$R_r^{p+} = R_{r1}^{(p1)+} + R_{r2}^{(p2)+} + R_{r3}^{(p3)+} + \ldots$$

the weighted average valence "p" is given by:

$$p = \frac{r1 \cdot p1 + r2 \cdot p2 + r3 \cdot p3 + \ldots}{r1 + r2 + r3 + \ldots}$$

It has also been noted that in the MeAPO-81 materials of this invention that a portion of $M^{2+}$ may also reside in the pores, likely in a charge balancing role.

The microporous crystalline metallophosphate MeAPO-81 is prepared by a hydrothermal crystallization of a reaction mixture prepared by combining reactive sources of R, A, E, phosphorous and M. A preferred form of the MeAPO-81 materials is when E is Al. The sources of aluminum include but are not limited to aluminum alkoxides, precipitated aluminas, aluminum metal, aluminum hydroxide, aluminum salts, alkali aluminates and alumina sols. Specific examples of aluminum alkoxides include, but are not limited to aluminum ortho sec-butoxide and aluminum ortho isopropoxide. Sources of phosphorus include, but are not limited to, orthophosphoric acid, phosphorus pentoxide, and ammonium dihydrogen phosphate. Sources of M include but are not limited to zinc acetate, zinc chloride, zinc oxide, cobalt acetate, cobalt chloride, magnesium acetate, magnesium nitrate, manganese sulfate, manganese acetate and manganese nitrate. Sources of the other E elements include but are not limited to precipitated gallium hydroxide, gallium chloride, gallium sulfate or gallium nitrate. Sources of the A metals include the halide salts, nitrate salts, hydroxide salts, acetate salts, and sulfate salts of the respective alkali metals. R is at least one quaternary organoammonium cation where at least one of the organoammonium cations is a cyclic diquaternary organoammonium cation, the quaternary ammonium cations selected from the group consisting of N,N,N',N'-tetramethyl-N,N'-p-xyleno-1,6-hexanediammonium, N,N,N',N'-tetramethyl-N,N'-butano-1,6-hexanediammonium, N,N,N',N'-tetrmaethyl-N,N'-hexano-1,6-hexanediammonium, N,N,N',N'-tetraethyl-N,N'-hexano-1,5-pentanediammonium, N,N,N',N'-tetramethyl-N,N'-m-xyleno-1,6-hexanediammonium, N,N,N',N'-tetramethyl-N,N'-o-xyleno-1,2-ethylenediammonium, N,N,N',N'-tetramethyl-N,N'-butano-1,2-ethylenediammonium, N,N,N',N'-tetramethyl-N,N'-butano-1,2-ethylenediammonium, tetramethylammonium (TMA$^+$), ethyltrimethylammonium (ETMA$^+$), diethyldimethylammonium (DEDMA$^+$), methyltriethylammonium (MTEA$^+$), dipropyldimethylammonium (DPDMA+), tetraethylammonium (TEA), tetrapropylammonium (TPA$^+$), tetrabutylammonium (TBA$^+$) and mixtures thereof, and the sources include the hydroxide, chloride, bromide, iodide and fluoride compounds. Specific examples include without limitation N,N,N',N'-tetramethyl-N,N'-p-xyleno-1,6-hexanediammonium dibromide, N,N,N',N'-tetramethyl-N,N'-p-xyleno-1,6-hexanediammonium dihydroxide, N,N,N',N'-tetramethyl-N,N'-butano-1,6-hexanediammonium dibromide, N,N,N',N'-tetrmaethyl-N,N'-hexano-1,6-hexanediammonium dibromide, tetrapropylammonium hydroxide, methyltriethylammonium hydroxide, tetraethylammonium hydroxide, and tetrabutylammonium hydroxide. In one embodiment R is a combination of N,N,N',N'-tetramethyl-N,N'-p-xyleno-1,6-hexanediammonium and TPA$^+$. In another embodiment, R is a combination of N,N,N',N'-tetramethyl-N,N'-butano-1,6-hexanediammonium and TPA$^+$. In yet another embodiment, R is a combination of N,N,N',N'-tetramethyl-N,N'-hexano-1,6-hexanediammonium and TPA$^+$.

The reaction mixture containing reactive sources of the desired components can be described in terms of molar ratios of the oxides by the formula:

$$aR_{2/p}O: bA_2O: cMO:E_2O_3:dP_2O_5:eH_2O$$

where "a" varies from about 2.1 to about 100, "b" varies from about 0.1 to about 8, "c" varies from about 0.25 to about 8, "d" varies from about 1.69 to about 25, and "e"

varies from 30 to 5000. If alkoxides are used, it is preferred to include a distillation or evaporative step to remove the alcohol hydrolysis products. The reaction mixture is now reacted at a temperature of about 60° to about 200° C. and preferably from about 95° to about 175° C. for a period of about 1 day to about 3 weeks and more preferably for a time of about 1 day to about 7 days in a sealed reaction vessel at autogenous pressure. After crystallization is complete, the solid product is isolated from the heterogeneous mixture by means such as filtration or centrifugation, and then washed with deionized water and dried in air at ambient temperature up to about 100° C. MeAPO-81 seeds can optionally be added to the reaction mixture in order to accelerate or otherwise enhance the formation of the desired microporous composition.

A favored approach to MeAPO-81 synthesis is the Charge Density Mismatch Approach, which has been applied to the synthesis of aluminosilicate zeolites, as outlined in U.S. Pat. No. 7,578,993 and in CHEM. MATER., 2014, 26, 6684-6694. It is applied to metalloaluminophosphates for the first time here. Metalloaluminophosphate solutions are prepared with excess phosphate and large, low charge density SDAs, such as TPAOH, TEAOH, and TBAOH, which are then perturbed by the addition of small amounts of alkali and cyclic diquaternary organoammonium to induce crystallization under the synthesis conditions. The method has advantages in expense and efficiency because the non-commercially available cyclic diquaternary organoammonium cations can be utilized in small amounts and they don't have to be converted to the hydroxide form, an additional expensive step, for use.

The MeAPO-81 metallophosphate-based material, which is obtained from the above-described process, is characterized by the x-ray diffraction pattern, having at least the d-spacings and relative intensities set forth in Table A below.

TABLE A

| 2Θ | d(Å) | I/I$_0$ % |
|---|---|---|
| 6.83-6.64 | 12.94-13.30 | m-s |
| 7.69-7.49 | 11.48-11.80 | vs-vs |
| 10.12-10.02 | 8.73-8.82 | w |
| 13.24-13.01 | 6.68-6.80 | w-m |
| 14.90-14.63 | 5.94-6.05 | w-m |
| 15.48-15.34 | 5.72-5.77 | w-m |
| 16.70-16.45 | 5.305-5.385 | w |
| 18.99-18.67 | 4.67-4.75 | w-m |
| 20.31-20.07 | 4.37-4.42 | m-s |
| 21.32-21.01 | 4.165-4.225 | m-s |
| 23.97-23.64 | 3.71-3.76 | w-m |
| 24.33-24.00 | 3.655-3.705 | m-vs |
| 26.71-26.35 | 3.335-3.38 | m |
| 27.51-27.00 | 3.24-3.30 | w-m |
| 27.68-27.25 | 3.22-3.27 | w-m |
| 28.78-28.31 | 3.10-3.15 | w-m |
| 29.86-29.50 | 2.99-3.025 | m-s |
| 30.38-29.96 | 2.94-2.98 | m-s |
| 30.70-30.27 | 2.91-2.95 | m |
| 33.60-33.03 | 2.665-2.71 | m |
| 34.13-33.73 | 2.625-2.655 | m |
| 35.35-34.84 | 2.537-2.573 | w-m |

The MeAPO-81 material may be modified in many ways to tailor it for use in a particular application. Modifications include calcination, ammonia calcinations, ion-exchange, steaming, various acid extractions, ammonium hexafluorosilicate treatment, or any combination thereof, some of which are outlined for the case of UZM-4 in U.S. Pat. No. 6,776,975 B1 which is incorporated by reference in its entirety. In addition, properties that may be modified include porosity, adsorption, framework composition, acidity, thermal stability, ion-exchange capacity, etc.

As synthesized, the MeAPO-81 material will contain some of the exchangeable or charge balancing cations in its pores. These exchangeable cations can be exchanged for other cations, or in the case of organic cations, they can be removed by heating under controlled conditions. Because MeAPO-81 is a large pore material, the BPH structure has 12-ring pores along the c-axis, many organic cations may be removed directly by ion-exchange, heating may not be necessary. If heating is required to remove the organic cations from the pores, a preferred method is ammonia calcination. Calcination in air converts the organic cations in the pores to protons, which can lead to the loss of some metal, for Example Al, from the framework upon exposure to ambient atmospheric water vapor. When the calcination is carried out in an ammonia atmosphere, the organic cation in the pore is replaced by $NH_4^+$ cation and the framework remains intact (see STUDIES IN SURFACE SCIENCE, (2004) vol. 154, p. 1324-1331). Typical conditions for ammonia calcinations include the use of gaseous anhydrous ammonia flowing at a rate of 1.1 Umin while ramping the sample temperature at 5° C./min to 500° C. and holding at that temperature for a time ranging from 5 minutes to an hour. The resulting ammonium/alkali form of MeAPO-81 has essentially the diffraction pattern of Table A. Once in this form, the ammonia calcined material may be ion-exchanged with $H^+$, $NH_4^+$, alkali metals, alkaline earth metals, transition metals, rare earth metals, or any mixture thereof, to achieve a wide variety of compositions with the MeAPO-81 framework in superior condition.

When MeAPO-81 or its modified forms are calcined in air, there can be a loss of metal from the framework, such as Al, which can alter the x-ray diffraction pattern from that observed for the as-synthesized MeAPO-81 (see STUDIES IN SURFACE SCIENCE, (2004) vol. 154, p. 1324-1331). Typical conditions for the calcination of the MeAPO-81 sample include ramping the temperature from room temperature to a calcination temperature of 400° to 600° C., preferably a calcination temperature of 450° to 550° C. at a ramp rate of 1 to 5° C./min, preferably a ramp rate of 2 to 4° C./min, the temperature ramp conducted in an atmosphere consisting either of flowing nitrogen or flowing clean dry air, preferably an atmosphere of flowing nitrogen. Once at the desired calcination temperature, if the calcination atmosphere employed during the temperature ramp is flowing clean dry air, it may remain flowing clean dry air. If the calcination atmosphere during the ramp was flowing nitrogen, it may remain flowing nitrogen at the calcination temperature or it may be immediately converted to clean dry air; preferably at the calcination temperature the calcination atmosphere will remain flowing nitrogen for a period of 1 to 10 hours and preferably for a period of 2 to 4 hours before converting the calcination atmosphere to flowing clean dry air. The final step of the calcination is a dwell at the calcination temperature in clean dry air. Whether the calcination atmosphere during the initial temperature ramp was flowing nitrogen or flowing clean dry air, once at the calcination temperature and once the calcination atmosphere is clean dry air, the MeAPO-81 sample will spend a period of 1 to 24 hours and preferably a period of 2 to 6 hours under these conditions to complete the calcination process.

The crystalline MeAPO-81 materials of this invention can be used for separating mixtures of molecular species, removing contaminants through ion exchange and catalyzing various hydrocarbon conversion processes. Separation of molecular species can be based either on the molecular size (kinetic diameter) or on the degree of polarity of the molecular species.

Methods used to exchange one cation for another are well known in the art and involve contacting the microporous compositions with a solution containing the desired cation (at molar excess) at exchange conditions. Exchange conditions include a temperature of about 15° C. to about 100° C. and a time of about 20 minutes to about 50 hours. Although not preferred, the organic cation can first be removed by heating under controlled conditions.

The MeAPO-81 compositions of this invention can also be used as a catalyst or catalyst support in various hydrocarbon conversion processes. Hydrocarbon conversion processes are well known in the art and include cracking, hydrocracking, alkylation of both aromatics and isoparaffin, isomerization, polymerization, reforming, hydrogenation, dehydrogenation, transalkylation, dealkylation, hydration, dehydration, hydrotreating, hydrodenitrogenation, hydrodesulfurization, methanol to olefins, methanation and syngas shift process. Specific reaction conditions and the types of feeds which can be used in these processes are set forth in U.S. Pat. Nos. 4,310,440, 4,440,871 and 5,126,308, which are incorporated by reference. Preferred hydrocarbon conversion processes are those in which hydrogen is a component such as hydrotreating or hydrofining, hydrogenation, hydrocracking, hydrodenitrogenation, hydrodesulfurization, etc.

Hydrocracking conditions typically include a temperature in the range of 400° to 1200° F. (204° to 649° C.), preferably between 600° and 950° F. (316° and 510° C.). Reaction pressures are in the range of atmospheric to about 3,500 psig (24,132 kPag), preferably between 200 and 3000 psig (1379 and 20,685 kPag). Contact times usually correspond to liquid hourly space velocities (LHSV) in the range of about 0.1 to 15 $hr^{-1}$, preferably between about 0.2 and 3 $hr^{-1}$. Hydrogen circulation rates are in the range of 1,000 to 50,000 standard cubic feet (scf) per barrel of charge (178 to 8,888 std. $m^3/m^3$), preferably between 2,000 and 30,000 scf per barrel of charge (355 and 5,333 std. $m^3/m^3$). Suitable hydrotreating conditions are generally within the broad ranges of hydrocracking conditions set out above.

The reaction zone effluent is normally removed from the catalyst bed, subjected to partial condensation and vapor-liquid separation and then fractionated to recover the various components thereof. The hydrogen, and if desired some or all of the unconverted heavier materials, are recycled to the reactor. Alternatively, a two-stage flow may be employed with the unconverted material being passed into a second reactor. Catalysts of the subject invention may be used in just one stage of such a process or may be used in both reactor stages.

Catalytic cracking processes are preferably carried out with the MeAPO-81 composition using feedstocks such as gas oils, heavy naphthas, deasphalted crude oil residua, etc. with gasoline being the principal desired product. Temperature conditions of 850° to 1100° F. (455° to 593° C.), LHSV values of 0.5 to 10 $hr^{-1}$ and pressure conditions of from about 0 to 50 psig (0 to 345 kPa) are suitable.

Alkylation of aromatics usually involves reacting an aromatic ($C_2$ to $C_{12}$), especially benzene, with a monoolefin to produce a linear alkyl substituted aromatic. The process is carried out at an aromatic:olefin (e.g., benzene:olefin) ratio of between 5:1 and 30:1, a LHSV of about 0.3 to about 6 $hr^{-1}$, a temperature of about 100° to about 250° C. and pressures of about 200 to about 1000 psig (1,379 to 6,895 kPa). Further details on apparatus may be found in U.S. Pat. No. 4,870,222 which is incorporated by reference.

Alkylation of isoparaffins with olefins to produce alkylates suitable as motor fuel components is carried out at temperatures of −30° to 40° C., pressures from about atmospheric to about 6,894 kPa (1,000 psig) and a weight hourly space velocity (WHSV) of 0.1 to about 120 $hi^{-1}$. Details on paraffin alkylation may be found in U.S. Pat. Nos. 5,157,196 and 5,157,197, which are incorporated by reference.

The conversion of methanol to olefins is effected by contacting the methanol with the MeAPO-81 catalyst at conversion conditions, thereby forming the desired olefins. The methanol can be in the liquid or vapor phase with the vapor phase being preferred. Contacting the methanol with the MeAPO-81 catalyst can be done in a continuous mode or a batch mode with a continuous mode being preferred. The amount of time that the methanol is in contact with the MeAPO-81 catalyst must be sufficient to convert the methanol to the desired light olefin products. When the process is carried out in a batch process, the contact time varies from about 0.001 hour to about 1 hour and preferably from about 0.01 hour to about 1.0 hour. The longer contact times are used at lower temperatures while shorter times are used at higher temperatures. Further, when the process is carried out in a continuous mode, the Weight Hourly Space Velocity (WHSV) based on methanol can vary from about 1 to about 1000 $hr^{-1}$ and preferably from about 1 to about 100 $hr^{-1}$.

Generally, the process must be carried out at elevated temperatures in order to form light olefins at a fast enough rate. Thus, the process should be carried out at a temperature of about 300° to about 600° C., preferably from about 400° to about 550° C. and most preferably from about 450° to about 525° C. The process may be carried out over a wide range of pressure including autogenous pressure. Thus, the pressure can vary from about 0 kPa (0 psig) to about 1724 kPa (250 psig) and preferably from about 34 kPa (5 psig) to about 345 kPa (50 psig).

Optionally, the methanol feedstock may be diluted with an inert diluent in order to more efficiently convert the methanol to olefins. Examples of the diluents which may be used are helium, argon, nitrogen, carbon monoxide, carbon dioxide, hydrogen, steam, paraffinic hydrocarbons, e. g., methane, aromatic hydrocarbons, e. g., benzene, toluene and mixtures thereof. The amount of diluent used can vary considerably and is usually from about 5 to about 90 mole percent of the feedstock and preferably from about 25 to about 75 mole percent.

The actual configuration of the reaction zone may be any well known catalyst reaction apparatus known in the art. Thus, a single reaction zone or a number of zones arranged in series or parallel may be used. In such reaction zones the methanol feedstock is flowed through a bed containing the MeAPO-81 catalyst. When multiple reaction zones are used, one or more MeAPO-81 catalysts may be used in series to produce the desired product mixture. Instead of a fixed bed, a dynamic bed system, e. g., fluidized or moving, may be used. Such a dynamic system would facilitate any regeneration of the MeAPO-81 catalyst that may be required. If regeneration is required, the MeAPO-81 catalyst can be continuously introduced as a moving bed to a regeneration zone where it can be regenerated by means such as oxidation in an oxygen containing atmosphere to remove carbonaceous materials.

The following examples are presented in illustration of this invention and are not intended as undue limitations on the generally broad scope of the invention as set out in the appended claims. The products of this invention are designated with the general name MeAPO-81, with the understanding that all of the MeAPO-81 materials exhibit a structure with the BPH topology.

The structure of the MeAPO-81 compositions of this invention was determined by x-ray analysis. The x-ray patterns presented in the following examples were obtained using standard x-ray powder diffraction techniques. The radiation source was a high-intensity, x-ray tube operated at 45 kV and 35 mA. The diffraction pattern from the copper K-alpha radiation was obtained by appropriate computer based techniques. Flat compressed powder samples were continuously scanned at 2° to 56° (2θ). Interplanar spacings (d) in Angstrom units were obtained from the position of the diffraction peaks expressed as θ where θ is the Bragg angle as observed from digitized data. Intensities were determined from the integrated area of diffraction peaks after subtracting background, "$I_o$" being the intensity of the strongest line or peak, and "I" being the intensity of each of the other peaks.

As will be understood by those skilled in the art the determination of the parameter 2θ is subject to both human and mechanical error, which in combination can impose an uncertainty of about ±0.4° on each reported value of 2θ. This uncertainty is, of course, also manifested in the reported values of the d-spacings, which are calculated from the 2θ values. This imprecision is general throughout the art and is not sufficient to preclude the differentiation of the present crystalline materials from each other and from the compositions of the prior art. In some of the x-ray patterns reported, the relative intensities of the d-spacings are indicated by the notations vs, s, m, and w which represent very strong, strong, medium, and weak, respectively. In terms of 100× $I/I_o$, the above designations are defined as:

w=0-15; m=15-60; s=60-80 and vs=80-100

In certain instances the purity of a synthesized product may be assessed with reference to its x-ray powder diffraction pattern. Thus, for example, if a sample is stated to be pure, it is intended only that the x-ray pattern of the sample is free of lines attributable to crystalline impurities, not that there are no amorphous materials present.

In order to more fully illustrate the invention, the following examples are set forth. It is to be understood that the examples are only by way of illustration and are not intended as an undue limitation on the broad scope of the invention as set forth in the appended claims.

Examples 1-3

Examples 1-3 cover the synthesis of the cyclic diquats structure directing agents SDA1, SDA2 and SDA3 that are utilized in the Charge Density Mismatch syntheses of MeAPO-81 in Examples 4-6.

Example 1: Synthesis of SDA1

N,N,N',N'-tetramethyl-N,N'-p-xyleno-1,6-hexanediammonium dibromide

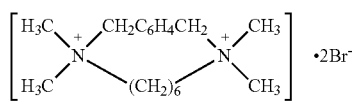

A 50.00 g portion of α,α' dibromo-p-xylene (Sigma-Aldrich) was placed in a 1-liter beaker and dissolved in 550 ml dry tetrahydrofuran (THF) using a stirbar. The resulting solution was transferred to a 1 liter 3-neck round bottom flask equipped with an overhead stirrer, a heating mantle and a reflux condenser. Separately, 33.31 g N,N,N',N'-tetramethyl-1,6-hexanediamine (99%, Sigma-Aldrich) was diluted with 32.50 g THF and placed in a pressure-equalizing dropping funnel that was attached to one of the necks of the round bottom flask. The amine solution was then added dropwise to the dibromide solution in the flask with stirring. Some solid formation was observed during the addition. Upon completion of the addition, the dropping funnel was removed and a thermocouple connected to a temperature controller was inserted into the flask. After stirring for 15 minutes, the reaction mixture was heated to 64° C. and held at that temperature for 42 hours. The reaction was allowed to cool and the solid product was isolated by filtration under a nitrogen blanket. The solid was washed with ether and filtered under nitrogen blanket before residual solvent was removed using a vacuum oven. The identity of cyclic diquat SDA1, N,N,N',N'-tetramethyl-N,N'-p-xyleno-1,6-hexanediammonium dibromide, in which two dimethyl-substituted quaternized N-atoms are attached by 1) a $(CH_2)_6$ chain and 2) a p-xylyl group, was confirmed by $^{13}C$ nmr as there was excellent agreement between observed and calculated nmr line positions.

Example 2: Synthesis of SDA2

N,N,N',N'-tetramethyl-N,N'-butano-1,6-hexanediammonium dibromide

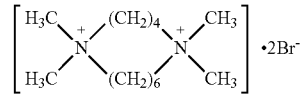

A 85.00 g portion N,N,N',N'-tetramethyl-1,6-hexanediamine (99%) was diluted in 500 ml dry tetrahydrofuran (THF) in 1-liter beaker using a stirbar. The resulting solution was transferred to a 1 liter 3-neck round bottom flask equipped with an overhead stirrer, a heating mantle and a reflux condenser. Separately, 106.51 g 1,4-dibromobutane (99.1%, Sigma-Aldrich) was placed in a pressure-equalizing dropping funnel that was attached to one of the necks of the round bottom flask. The dibromide was then added to the amine solution in the flask in a dropwise fashion with stirring. The reaction mixture remained a solution over the course of the addition. Upon completion of the addition, the dropping funnel was removed and a thermocouple connected to a temperature controller was inserted into the flask. After stirring for 30 minutes, there was no visible reaction, the reaction mixture was still a solution. The reaction mixture was heated to 64° C. and held at that temperature for 24 hours. Solid formation in the reaction mixture started to become visible once the reaction reached 40° C. Once completed, the reaction was allowed to cool and the solid product was isolated by filtration under a nitrogen blanket. The solid was washed with ether and filtered under nitrogen blanket before residual solvent was removed using a vacuum oven. The identity of cyclic diquat SDA2, N,N,N',N'-tetramethyl-N,N'-butano-1,6-hexanediammonium dibromide, in which two dimethyl-substituted quaternized N-atoms are attached by 1) a $(CH_2)_6$ chain and 2) a $(CH_2)_4$ chain, was

Example 3: Synthesis of SDA3

N,N,N',N'-tetramethyl-N,N'-hexano-1,6-hexanediammonium dibromide

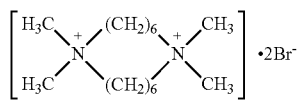

A 60.00 g portion of 1,6-dibromohexane (96%, Sigma-Aldrich) was placed in a 1-liter beaker and dissolved in 500 ml dry tetrahydrofuran (THF) using a stirbar. The resulting solution was transferred to a 1 liter 3-neck round bottom flask equipped with an overhead stirrer, a heating mantle and a reflux condenser. Separately, 41.09 g N,N,N',N'-tetramethyl-1,6-hexanediamine (99%, Sigma-Aldrich) was diluted with 50 ml THF and placed in a pressure-equalizing dropping funnel that was attached to one of the necks of the round bottom flask. The amine solution was then added dropwise to the dibromide solution in the flask, but quickly, with stirring, resulting in a clear solution. Upon completion of the addition, the dropping funnel was removed and a thermocouple connected to a temperature controller was inserted into the flask. The reaction mixture was then heated to 64° C. and held at that temperature for 21 hours. The final reaction mixture consisted of a voluminous white solid suspended in the liquid. The reaction was allowed to cool and the solid product was isolated by filtration under a nitrogen blanket. The solid was washed with ether and filtered under nitrogen blanket before residual solvent was removed using a vacuum oven. The identity of cyclic diquat SDA3, N,N,N',N'-tetramethyl-N,N'-hexano-1,6-hexanediammonium dibromide, in which two dimethyl-substituted quaternized N-atoms are attached to each other by 1) a $(CH_2)_6$ chain and 2) another $(CH_2)_6$ chain, was confirmed by $^{13}C$ nmr as there was excellent agreement between observed and calculated nmr line positions.

Example 4

A Teflon beaker was charged with 130.00 g tetrapropylammonium hydroxide (TPAOH, 40%, SACHEM, Inc.) and placed under a high speed overhead stirrer. Then pre-ground aluminum isopropoxide (Sigma-Aldrich, 13.2% Al), 5.23 g was added and dissolved with stirring. Then 17.54 g $H_3PO_4$ (85.7%) was added dropwise to the reaction mixture with continued stirring, yielding a clear solution. Separately, 5.61 g $Zn(OAc)_2 \cdot 2H_2O$ (Sigma-Aldrich) was dissolved in 25.00 g deionized water. This solution was added fast dropwise to the reaction mixture with stirring, forming a clear solution within five minutes. The reaction mixture was diluted further with 15.00 g deionized water. Separately, 5.58 g of the cyclic diquat SDA1 from Example 1 was dissolved in 33.00 g deionized water. This was added dropwise to the reaction mixture, which induced solid formation immediately and formed a white suspension by the end of the addition. Separately, KOAc (Sigma-Aldrich, 99.4%), 1.26 g, was dissolved in 10.00 g deionized water. This solution was added dropwise to the white gel/suspension. After further homogenization, the reaction mixture was distributed among seven Teflon-lined autoclaves, which were digested quiescently at 95°, 125°, 150°, and 175° C. for either 66 or 189 hours or both at autogenous pressure. The solid products were isolated by centrifugation, washed with deionized water and dried at room temperature. All of the reactions yielded MeAPO-81 products with the BPH topology as determined by powder x-ray diffraction. Representative x-ray diffraction lines observed for the 175° C./189 hours product are given in Table 1. Scanning Electron Microscopic (SEM) analysis of this product showed the crystals to consist of thin rounded hexagonal plates, 0.2 to 0.8μ across and less than about 100 nm thick. Elemental analysis on this same product yielded the stoichiometry $N_{0.31}K_{0.24}Zn_{0.51}Al_{0.51}P$.

TABLE 1

| 2-Θ | d(Å) | I/I₀ % |
|---|---|---|
| 6.70 | 13.18 | s |
| 7.56 | 11.69 | vs |
| 10.08 | 8.77 | w |
| 13.12 | 6.74 | m |
| 13.40 | 6.60 | m |
| 14.74 | 6.00 | w |
| 15.07 | 5.88 | w |
| 15.40 | 5.75 | m |
| 16.55 | 5.35 | w |
| 18.82 | 4.71 | m |
| 20.22 | 4.39 | s |
| 21.18 | 4.19 | s |
| 23.82 | 3.73 | m |
| 24.14 | 3.68 | vs |
| 26.54 | 3.36 | m |
| 27.26 | 3.27 | m |
| 27.46 | 3.24 | w |
| 28.30 | 3.15 | m |
| 28.62 | 3.12 | m |
| 29.70 | 3.01 | m |
| 30.16 | 2.96 | m |
| 30.56 | 2.92 | m |
| 33.36 | 2.68 | m |
| 33.90 | 2.64 | m |
| 35.12 | 2.55 | m |
| 36.58 | 2.45 | w |
| 38.12 | 2.36 | w |
| 38.88 | 2.31 | w |
| 40.02 | 2.25 | w |
| 40.86 | 2.21 | w |
| 43.02 | 2.10 | m |

Example 5

A Teflon beaker was charged with 130.00 g tetrapropylammonium hydroxide (TPAOH, 40%, SACHEM Inc.) and placed under a high speed overhead stirrer. Then pre-ground aluminum isopropoxide (Sigma-Aldrich, 13.2% Al), 5.23 g was added and dissolved with stirring. Then 17.54 g $H_3PO_4$ (85.7%) was added dropwise to the reaction mixture with continued stirring, yielding a clear solution. Separately, 5.61 g $Zn(OAc)_2 \cdot 2H_2O$ (Sigma-Aldrich) was dissolved in 25.00 g deionized water. This solution was added fast dropwise to the reaction mixture with stirring, forming a clear solution within five minutes. The reaction mixture was diluted further with 15.00 g deionized water. Separately, 4.96 g of the cyclic diquat SDA2 from Example 2 was dissolved in 33.00 g deionized water. This was added dropwise to the reaction mixture, which induced solid formation immediately and formed a white suspension by the end of the reaction. Separately, KOAc (Sigma-Aldrich, 99.4%), 1.26 g, was dissolved in 10.00 g deionized water. This solution was added dropwise to the white gel/suspension. The reaction mixture was distributed among seven Teflon-lined autoclaves, which were digested quiescently at 95°, 125°, 150°, and 175° C. for either 66 or 188 hours at autogenous pressure. The solid products were isolated by centrifugation, washed with deionized water and dried at room temperature. Powder x-ray diffraction showed all products contained MeAPO-81 with the BPH topology as the major product and several of the products were pure MeAPO-81. Representative x-ray diffraction lines are presented for the pure MeAPO-81 product isolated from the 150° C./66 hours digestion in Table 2 below. Elemental analysis performed on this same sample yielded the stoichiometry $N_xK_{0.22}Zn_{0.52}Al_{0.47}P$.

TABLE 2

| 2-Θ | d(Å) | $I/I_0$ % |
|---|---|---|
| 6.76 | 13.07 | m |
| 7.64 | 11.57 | vs |
| 10.08 | 8.76 | w |
| 13.17 | 6.71 | m |
| 14.82 | 5.97 | w |
| 15.42 | 5.74 | m |
| 16.63 | 5.33 | w |
| 18.88 | 4.70 | w |
| 20.16 | 4.40 | m |
| 21.22 | 4.18 | s |
| 23.86 | 3.73 | m |
| 24.24 | 3.67 | s |
| 26.58 | 3.35 | m |
| 27.34 | 3.26 | m |
| 27.54 | 3.24 | m |
| 28.46 | 3.13 | w |
| 29.76 | 3.00 | m |
| 30.26 | 2.95 | m |
| 30.64 | 2.92 | m |
| 30.74 | 2.91 | m |
| 33.45 | 2.68 | m |
| 34.02 | 2.63 | m |
| 35.21 | 2.55 | w |

Example 6

A 3 liter beaker was charged with 1000.00 g TPAOH (40%) and placed under a high speed overhead stirrer. Pre-ground aluminum isopropoxide (13.2% Al), 40.21 g, was added and dissolved with stirring. The reaction mixture was then diluted with 600.00 g deionized water. Then 134.97 g $H_3PO_4$ (85.7%) was added in a single slow pour with stirring, followed by the addition of 50.00 g deionized water. Separately, 43.18 g $Zn(OAc)_2 \cdot 2H_2O$ was dissolved in 173.84 g deionized water. This solution was added to the reaction mixture in a dropwise fashion intermittently with vigorous stirring. With continued homogenization, a clear solution results. The final solution weight was 2012.1 g.

A 180.00 g portion of this TPA$^+$-Zn—Al—P solution was placed in a Teflon beaker positioned under a high speed overhead stirrer. Separately, 0.86 g KOAc (99.4%) and 7.33 g SDA3 from Example 3 were dissolved in 45.00 g deionized water. This solution was added to the reaction mixture dropwise, inducing solid formation with the first few drops. By the end of the addition the reaction mixture was an opaque white gel suspension. The reaction mixture was distributed among seven Teflon-lined autoclaves, which were digested quiescently at 95°, 125°, 150°, and 175° C. for either 52 or 167 hours at autogenous pressure. The solid products were isolated by centrifugation, washed with deionized water and dried at room temperature. Powder x-ray diffraction showed all products contained MeAPO-81 with the BPH topology as the major product and all of the products synthesized at 150° and 175° C. were pure MeAPO-81. Representative x-ray diffraction lines are given in Table 3 below for the product resulting from the 175° C./52 hours digestion. Elemental analysis showed this same material to have the stoichiometry $N_{0.32}K_{0.26}Zn_{0.58}Al_{0.45}P$.

TABLE 3

| 2-Θ | d(Å) | $I/I_0$ % |
|---|---|---|
| 6.70 | 13.18 | s |
| 7.54 | 11.72 | vs |
| 10.06 | 8.78 | w |
| 13.06 | 6.77 | w |
| 13.39 | 6.61 | w |
| 14.71 | 6.02 | w |
| 15.40 | 5.75 | m |
| 16.51 | 5.36 | w |
| 18.76 | 4.73 | m |
| 20.00 | 4.44 | m |
| 20.16 | 4.40 | m |
| 21.10 | 4.21 | m |
| 23.72 | 3.75 | w |
| 24.1 | 3.69 | s |
| 26.47 | 3.36 | m |
| 27.14 | 3.28 | w |
| 27.38 | 3.26 | w |
| 28.20 | 3.16 | w |
| 28.54 | 3.13 | m |
| 29.60 | 3.02 | m |
| 30.09 | 2.97 | m |
| 30.44 | 2.93 | m |
| 33.22 | 2.69 | m |
| 33.82 | 2.65 | m |
| 34.98 | 2.56 | w |
| 35.67 | 2.51 | w |
| 36.46 | 2.46 | w |
| 37.97 | 2.37 | w |
| 39.66 | 2.27 | w |
| 40.64 | 2.22 | w |
| 42.84 | 2.11 | w |
| 43.36 | 2.09 | w |
| 49.40 | 1.84 | w |
| 50.15 | 1.82 | w |

The invention claimed is:

1. A microporous crystalline metallophosphate material having a three-dimensional framework of $[M^{2+}O_{4/2}]^{2-}$, $[EO_{4/2}]^-$ and $[PO_{4/2}]^+$ and tetrahedral units and an empirical composition in the as synthesized form and on an anhydrous basis expressed by an empirical formula of:

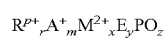

where R is at least one quaternary organoammonium cation of which there must be at least one cyclic diquaternary organoammonium cation, the organoammonium cations selected from the group consisting of N,N,N',N'-tetramethyl-N,N'-p-xyleno-1,6-hexanediammonium, N,N,N',N'-tetramethyl-N,N'-butano-1,6-hexanediammonium, N,N,N',N'-tetramethyl-N,N'-hexano-1,6-hexanediammonium, N,N,N',N'-tetraethyl-N,N'-hexano-1,5-pentanediammonium, N,N,N',N'-tetramethyl-N,N'-m-xyleno-1,6-hexanediammonium, N,N,N',N'-tetramethyl-N,N'-o-xyleno-1,2-ethylenediammonium, N,N,N',N'-tetramethyl-N,N'-butano-1,2-ethylenediammonium, N,N,N',N'-tetramethyl-N,N'-butano-1,2-ethylenediammonium, tetramethylammonium (TMA$^+$), ethyltrimethylammonium (ETMA$^+$), diethyldimethylammonium (DEDMA$^+$), methyltriethylammonium (MTEA$^+$), dipropyldimethylammonium (DPDMA$^+$), tetraethylammonium (TEA$^+$), tetrapropylammonium (TPA$^+$), tetrabutylammonium (TBA$^+$) and mixtures thereof, "r" is the mole ratio of R to P and has a value of about 0.04 to about 1.0, "p" is the weighted average valence of R and varies from 1 to 2, A is an alkali metal selected from the group consisting of $Li^+$, $Na^+$, $K^+$, $Rb^+$ and $Cs^+$ and mixtures thereof, "m" is the mole ratio of A to P and varies from 0.1 to 1.0, M is a divalent element selected from the group of Zn, Mg, Co, Mn and mixtures thereof, "x" is the mole ratio of M to P and varies from 0.2 to about 0.9, E is a trivalent element selected from the group consisting of aluminum and gallium and mixtures thereof, "y" is the mole ratio of E to P and varies from 0.1 to about 0.8 and "z" is the mole ratio of O to P and has a value determined by the equation:

$$z=(m+p \cdot r+2 \cdot x+3 \cdot y+5)/2$$

and is characterized in that it has the x-ray diffraction pattern having at least the d-spacings and intensities set forth in Table A:

TABLE A

| 2Θ | d(Å) | $I/I_0$ % |
|---|---|---|
| 6.83-6.64 | 12.94-13.30 | m-s |
| 7.69-7.49 | 11.48-11.80 | vs-vs |
| 10.12-10.02 | 8.73-8.82 | w |
| 13.24-13.01 | 6.68-6.80 | w-m |
| 14.90-14.63 | 5.94-6.05 | w-m |
| 15.48-15.34 | 5.72-5.77 | w-m |
| 16.70-16.45 | 5.305-5.385 | w |
| 18.99-18.67 | 4.67-4.75 | w-m |
| 20.31-20.07 | 4.37-4.42 | m-s |
| 21.32-21.01 | 4.165-4.225 | m-s |
| 23.97-23.64 | 3.71-3.76 | w-m |
| 24.33-24.00 | 3.655-3.705 | m-vs |
| 26.71-26.35 | 3.335-3.38 | m |
| 27.51-27.00 | 3.24-3.30 | w-m |

TABLE A-continued

| 2Θ | d(Å) | $I/I_0$ % |
|---|---|---|
| 27.68-27.25 | 3.22-3.27 | w-m |
| 28.78-28.31 | 3.10-3.15 | w-m |
| 29.86-29.50 | 2.99-3.025 | m-s |
| 30.38-29.96 | 2.94-2.98 | m-s |
| 30.70-30.27 | 2.91-2.95 | m |
| 33.60-33.03 | 2.665-2.71 | m |
| 34.13-33.73 | 2.625-2.655 | m |
| 35.35-34.84 | 2.537-2.573 | w-m. |

2. The metallophosphate material of claim 1 where A is potassium.

3. The metallophosphate material of claim 1 where E is aluminum.

4. The metallophosphate material of claim 1 where R is at least N,N,N',N'-tetramethyl-N,N'-p-xyleno-1,6-hexanediammonium.

5. The metallophosphate material of claim 1 where R is at least N,N,N',N'-tetramethyl-N,N'-butano-1,6-hexanediammonium.

6. The metallophosphate material of claim 1 where R is at least N,N,N',N'-tetrmaethyl-N,N'-hexano-1,6-hexanediammonium.

7. A crystalline modified form of the crystalline microporous metallophosphate of claim 1, comprising a three-dimensional framework of $[M^{2+}O_{4/2}]^{2-}$, $[EO_{4/2}]^-$ and $[PO_{4/2}]^+$ tetrahedral units and derived by modifying the crystalline microporous metallophosphate of claim 1, the modifications including calcination, ammonia calcinations, ion-exchange, or any combination thereof.

* * * * *